(12) United States Patent
Yanagisawa et al.

(10) Patent No.: US 9,653,252 B2
(45) Date of Patent: *May 16, 2017

(54) X-RAY GENERATING TUBE, X-RAY GENERATING APPARATUS AND X-RAY IMAGING SYSTEM USING THE SAME

(71) Applicant: CANON KABUSHIKI KAISHA, Tokyo (JP)

(72) Inventors: Yoshihiro Yanagisawa, Fujisawa (JP); Yasue Sato, Machida (JP); Noritaka Ukiyo, Inagi (JP); Kazuhiro Sando, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/958,264

(22) Filed: Dec. 3, 2015

(65) Prior Publication Data

US 2016/0086761 A1    Mar. 24, 2016

Related U.S. Application Data

(63) Continuation of application No. 14/258,641, filed on Apr. 22, 2014, now Pat. No. 9,230,774.

(30) Foreign Application Priority Data

Jun. 5, 2013 (JP) ................................. 2013-118467
Nov. 29, 2013 (JP) ................................. 2013-246985

(51) Int. Cl.
*H01J 35/00* (2006.01)
*H01J 35/18* (2006.01)
(Continued)

(52) U.S. Cl.
CPC .............. *H01J 35/18* (2013.01); *G01N 23/04* (2013.01); *H01J 35/06* (2013.01); *H01J 35/08* (2013.01);
(Continued)

(58) Field of Classification Search
CPC G01N 23/04; H01J 2235/18; H01J 2235/186; H01J 35/06; H01J 35/08;
(Continued)

(56) References Cited

U.S. PATENT DOCUMENTS 9,230,774 B2 * 1/2016 Yanagisawa ............ H01J 35/18
2005/0213709 A1 * 9/2005 Dinsmore ............. H01J 35/065
378/119

(Continued)

FOREIGN PATENT DOCUMENTS

JP      2009-245806 A     10/2009

*Primary Examiner* — Irakli Kiknadze
(74) *Attorney, Agent, or Firm* — Fitzpatrick, Cella, Harper & Scinto

(57) ABSTRACT

Provided is an X-ray generating tube with improved withstand voltage property by a simple structure, the X-ray generating tube including a cathode connected to one opening of an insulating tube and an anode connected to the other opening, in which a resistive film having a lower sheet resistance value than that of the insulating tube is disposed on an outer periphery of the insulating tube, and the cathode and the anode are electrically connected to each other via the resistive film.

36 Claims, 5 Drawing Sheets

(51) Int. Cl.
*G01N 23/04* (2006.01)
*H01J 35/06* (2006.01)
*H01J 35/08* (2006.01)

(52) U.S. Cl.
CPC ..... *H01J 2235/18* (2013.01); *H01J 2235/186* (2013.01)

(58) Field of Classification Search
CPC .. H01J 35/18; H01J 35/065; H01J 9/24; H01J 2235/068; H01J 2235/087; H01J 35/14; H01J 2235/081; H01J 2235/20; H01J 35/16; H01J 35/32; H01J 2235/02; H01J 2235/086; C12Q 1/6883; C12Q 2600/118; C12Q 2600/156; C12Q 2600/158; H01L 51/5215; H01L 51/5231; H01L 51/5234; H01L 51/5262; H01L 51/5271; H01L 21/3081; H01L 31/109; H01L 21/312; H01L 27/00; H01L 31/032; H01L 31/18; C03C 17/2453; H01B 1/00; H01C 17/06; H01C 17/12; H01C 7/00

USPC .................................. 378/119, 140, 142, 145
See application file for complete search history.

(56) References Cited

U.S. PATENT DOCUMENTS

| | | |
|---|---|---|
| 2007/0230663 A1 | 10/2007 | Anno |
| 2010/0111265 A1 | 5/2010 | Holm et al. |
| 2011/0188635 A1 | 8/2011 | Cho et al. |
| 2012/0307974 A1 | 12/2012 | Yamazaki et al. |
| 2012/0314837 A1 | 12/2012 | Tsujii et al. |
| 2013/0016810 A1 | 1/2013 | Tamura et al. |
| 2013/0016811 A1 | 1/2013 | Ueda et al. |
| 2013/0016812 A1 | 1/2013 | Yanagisawa et al. |
| 2013/0034207 A1 | 2/2013 | Aoki et al. |
| 2013/0230143 A1 | 9/2013 | Ueda et al. |
| 2013/0235975 A1 | 9/2013 | Tamura et al. |
| 2014/0140480 A1 | 5/2014 | Ogura et al. |
| 2014/0140486 A1 | 5/2014 | Yanagisawa et al. |
| 2014/0153695 A1 | 6/2014 | Yanagisawa et al. |
| 2014/0177800 A1 | 6/2014 | Sato et al. |
| 2014/0369470 A1 | 12/2014 | Ukiyo et al. |

* cited by examiner

X-RAY GENERATING TUBE, X-RAY GENERATING APPARATUS AND X-RAY IMAGING SYSTEM USING THE SAME

The present application is a continuation of U.S. Application No. 14/258,641, filed on Apr. 22, 2014, which claims priority to JP 2013-246985 filed Nov. 29, 2013, and JP 2013-118467 filed Jun. 5, 2013, the entire disclosure of each of which is incorporated by reference herein.

BACKGROUND OF THE INVENTION

Field of the Invention

The present invention relates to an X-ray generating tube, and an X-ray generating apparatus and an X-ray imaging system including the X-ray generating tube, which can be used for a medical equipment, a nondestructive inspection apparatus, and the like, for example.

Description of the Related Art

In general, an X-ray generating tube accelerates electrons emitted from an electron emitting source with use of a tube voltage in a vacuum and irradiates a target made of a metal such as tungsten with the electron so as to generate X-ray. The tube voltage set in the X-ray generating tube is approximately 100 kV, for example, and the X-ray generating tube is required to have a structure that can withstand the high voltage.

In Japanese Patent Application Laid-Open No. 2009-245806, there is disclosed a technology for stably suppressing breakdown of a valve due to a discharge by applying an electrical resistive film onto an outer surface of the valve as an electrical insulation portion, in which the electrical resistive film is electrically connected to a case main body as an electrical conductive portion of the X-ray tube.

In the X-ray tube disclosed in Japanese Patent Application Laid-Open No. 2009-245806, the electrical resistive film is not applied onto a portion of the valve adjacent to a voltage application portion so as to maintain insulation of the valve. However, in this structure, in order to prevent a potential gradient in an area that is not covered with the electrical resistive film from being steep in a potential distribution on the outer surface of the valve, a complicated valve shape is required.

SUMMARY OF THE INVENTION

It is an object of the present invention to improve withstand voltage property of an X-ray generating tube by a simple structure, and further to provide an X-ray generating apparatus and an X-ray imaging system having high reliability by using the X-ray generating tube having improved withstand voltage property.

According to a first embodiment of the present invention, there is provided an X-ray generating tube, including: an insulating tube; a cathode including an electron emitting source, the cathode covering one opening of the insulating tube so that a peripheral edge portion thereof is joined to an end surface of the one opening; an anode including a target, the anode covering the other opening of the insulating tube so that a peripheral edge portion thereof is joined to an end surface of the other opening; and a resistive film disposed on an outer periphery of the insulating tube, the resistive film having a smaller sheet resistance value than a sheet resistance value of the insulating tube. The cathode and the anode are electrically connected to each other via the resistive film. A dark current at 100° C. when a voltage of 100 kV is applied between the cathode and the anode is 0.1 µA or more to 10 µA or less.

According to a second embodiment of the present invention, there is provided an X-ray generating apparatus, including: the X-ray generating tube according to the first embodiment of the present invention; and a container for storing the X-ray generating tube. The container includes an emission window for emitting X-ray generated by the X-ray generating tube. A rest space inside the container storing the X-ray generating tube is filled with insulating liquid.

According to a third embodiment of the present invention, there is provided an X-ray imaging system, including: the X-ray generating apparatus according to the second embodiment of the present invention; an X-ray detecting device configured to detect X-ray emitted from the X-ray generating apparatus and passing through a subject to be investigated; and a control device configured to control the X-ray generating apparatus and the X-ray detecting device in a coordinated manner.

Further features of the present invention will become apparent from the following description of exemplary embodiments with reference to the attached drawings.

DESCRIPTION OF THE EMBODIMENTS

Figure 1A:
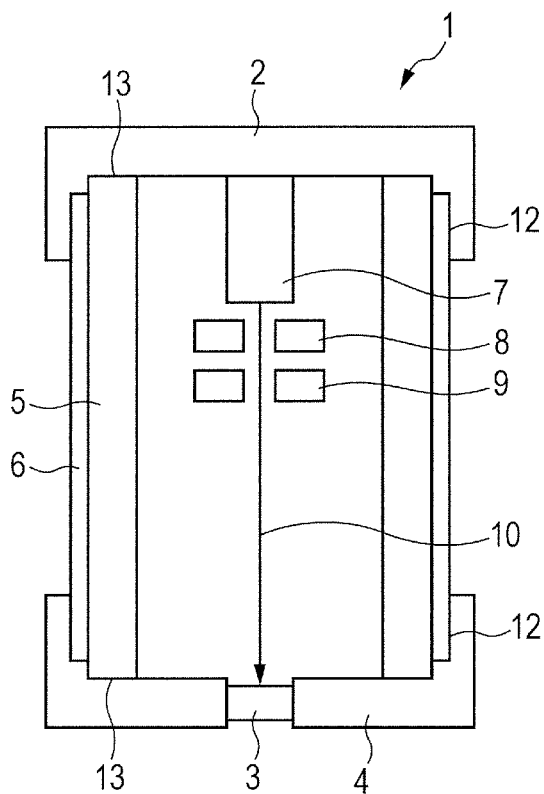
FIGS. 1A and 1B are schematic diagrams illustrating a structure of an X-ray generating tube according to an embodiment of the present invention.

Now, exemplary embodiments of the present invention are described in detail with reference to the attached drawings, but the present invention is not limited to these embodiments. In addition, a known or well-known technology in the art is applied to a portion that is not particularly illustrated or described in this specification. Further, in the drawings to be referred to below, the same numeral or symbol denotes the same component.

As illustrated in FIG. 1A, an X-ray generating tube 1 of the present invention basically includes an insulating tube 5, a cathode 2, and an anode 4. The cathode 2 covers one opening of the insulating tube 5, and a peripheral edge portion of the cathode 2 is joined to one end surface 13 of the insulating tube 5. The anode 4 covers the other opening of the insulating tube 5, and a peripheral edge portion of the anode 4 is joined to the other end surface 13 of the insulating tube 5. Further, the cathode 2 has an electron emitting source 7, and the anode 4 has a transmissive target 3. It can be said that the anode 4 forms an end window of the X-ray generating tube 1. A lens electrode 8 and an extraction electrode 9 are each connected to a power supply (not shown) so that a tube voltage of the X-ray generating tube 1 is defined.

As materials of the cathode 2 and the anode 4, there are Kovar, steel, steel alloy, SUS material, and a metal such as Ag, Cu, Ti, Mn, Mo, and Ni, and an alloy of these metals.

The insulating tube 5 is usually a cylindrical tube, but a tube having an elliptical or polygonal cross section may be used in the present invention. As a material of the insulating tube 5, there are so-called ceramic materials such as $Al_2O_3$ (alumina), $Si_3N_4$, SiC, AlN, and $ZrO_3$, but any insulation material may be used.

The cathode 2, the anode 4, and the insulating tube 5 are vacuum-tightly joined to each other so as to form a vacuum container. As joining means, brazing, welding, or the like can be used.

As the electron emitting source 7, a hot cathode such as a tungsten filament and an impregnated cathode, or a cold cathode such as a carbon nanotube can be used.

The target 3 may be made of a material that can emit X-rays by electron irradiation or may have a structure including an x-ray transmissive substrate and a target metal film formed thereon. As the x-ray transmissive substrate, it is preferred to use a substrate having strength capable of supporting the target metal, little absorption of X-rays generated by the target metal, and high thermal conductivity so that heat generated by the target metal can be rapidly dissipated. For instance, diamond, silicon carbide, aluminum nitride, or the like can be used.

As a material forming the target metal, it is preferred to use a material having a high melting point and high X-ray generation efficiency. For instance, tungsten, tantalum, molybdenum, or the like can be used. In order to reduce absorption that occurs when the generated X-ray passes through the target metal, it is appropriate that the target metal has a thickness of a few μm to ten and a few μm.

In the X-ray generating tube 1 of the present invention, a tube voltage is applied between the cathode 2 and the anode 4 by a high voltage power supply (not shown), and electrons generated by the electron emitting source 7 are drawn into vacuum by the extraction electrode 8. Then, the electrons are accelerated with the anode 4 whose potential is set to be positive of the tube voltage with respect to the cathode 2. Further, an electron beam 10 to be a tube current is converged by an action of the lens electrode 9, and the high energy electron beam 10 irradiates the target 3 made of a metal such as tungsten so that X-rays are generated.

The X-ray generating tube 1 of the present invention has a feature in that a resistive film 6 having a lower sheet resistance value than that of the insulating tube 5 is disposed on the outer periphery of the insulating tube 5, and that the resistive film 6 electrically connects the cathode 2 and the anode 4. With this structure, electrification of the surface caused in the related-art insulating tube 5 can be prevented, and an excessive potential gradient is not formed between the cathode 2 and the anode 4 so that discharge generated in the X-ray generating tube 1 is suppressed.

In the present invention, in order to obtain the effect of the resistive film 6, the resistive film 6 is formed so that a dark current becomes 0.1 μA or more to 10 μA or less at 100° C. when a voltage of 100 kV is applied between the cathode 2 and the anode 4. As a material of the resistive film 6, a glass material such as Kovar glass, glaze, and frit glass, or a metal oxide film can be used as long as a predetermined resistance can be obtained.

In the present invention, it is preferred that a specific resistance of the insulating tube 5 at 100° C. be $1 \times 10$ Ωm or more to $1 \times 10^{14}$ Ωm or less. Further, when the specific resistance of the insulating tube 5 falls within the above-mentioned range, it is preferred that $R_s2/R_s1$ be $1 \times 10^{-5}$ or more to $1 \times 10^{-1}$ or less, where $R_s1$ represents a sheet resistance value of the insulating tube 5 at 100° C., and $R_s2$ represents a sheet resistance value of the resistive film 6 at 100° C.

Next, the dark current flowing between the cathode 2 and the anode 4 at 100° C. and the sheet resistance values of the insulating tube 5 and the resistive film 6 at 100° C. defined in the present invention are calculated based on IV characteristics measured at multiple temperatures. A measuring method of the IV characteristics and a calculation method of the individual values are described below.

(1) A measuring electrode pair is a comb-like electrode pair having an electrode interval d of 50 μm, an electrode opposing section length L of 50 mm, and an electrode line width of 50 μm in an electrode opposing section. This comb-like electrode pair is formed on a surface of the resistive film 6 of the X-ray generating tube 1 for a measuring sample of the resistive film 6. In addition, the comb-like electrode pair is formed on an outer peripheral surface or an inner peripheral surface of the insulating tube 5 exposed by partially separating the resistive film 6 of the X-ray generating tube 1 for a measuring sample of the insulating tube 5. The measuring sample is placed in a chamber including a heat stage controlled by a temperature adjustment device and a measuring terminal connected to an IV measuring apparatus. The inside of the chamber can be vacuumed. Thermocouples connected to the temperature adjustment device are adhered onto the surface of the resistive film 6 and the surface of the insulating tube 5 on each of which the comb-like electrode pair is formed, by using a thermoset adhesive, and the comb-like electrode pair is connected to the measuring terminal of the chamber.

(2) The inside of the chamber is evacuated to a vacuum degree of $1 \times 10^{-4}$ Pa.

(3) The inside of the chamber is heated so that the measuring sample has 400° C. and is controlled so that the temperature is constant for 5 minutes. Next, in the constant temperature period, a voltage $V_{test}$ [V] is applied so as to measure a dark current I [A] flowing in the electrode pair. The voltage $V_{test}$ is determined by considering a distance D [m] between the cathode 2 and the anode 4, $V_a/D$ [V/m] determined by the tube voltage $V_a$ [V], and an inter-electrode distance d [m] between the comb-like electrodes. In the present invention, the tube voltage is set to $V_a=100 \times 10^3$ V.

The measurement described above is performed with a decreased temperature of 200° C. or 25° C. In this embodiment, the measurement is performed at three points while decreasing the temperature, but it is possible to perform the measurement while increasing the temperature. However, it is preferred to perform the measurement while decreasing the temperature because an influence of water adsorbed on the surface by bake effect can be reduced.

(4) An electrical conductivity σ(T) [S/m] is calculated based on the dark current I [A] obtained in (3) described above, a value of the applied voltage [V], and dimensions of a conductive path (the electrode interval d, the electrode length L, and the film thickness t [m] of the resistive film 6 and the insulating tube 5). Here, T represents an absolute temperature [K].

Electrical conductivities σ (673.15) at 400° C., σ (473.15) at 200° C., and σ (298.15) at 25° C. are determined based on σ(T)=(I(T)/V)×(d/(L×t)).

(5) Temperature dependence data of the electrical conductivity σ obtained in (4) described above is substituted into the following Arrhenius equation, to thereby determine, by using the least squares method, activation energy Ea [eV] of the electrical conductivity σ and an electrical conductivity $\sigma_0$ [S/m] under a theoretical temperature infinity condition.

$$\sigma(T)[S/m] = \sigma_0 \times \exp(-eE_a/kT)$$

In the above equation, e represents a unit charge (electron quantum, $1.9 \times 10^{-19}$ [C]), and k represents a Boltzmann constant ($1.38 \times 10^{-23}$ [J/K]).

An electrical conductivity σ (373.15) at 100° C. as an evaluation criterion in the present invention is determined, and is converted into $\sigma(T) = \sigma_s(T) \times t$ so as to determine a sheet electrical conductivity $\sigma_s$ [S·□] at 100° C. Further, the reciprocal of the sheet electrical conductivity $\sigma_s$ is determined as a sheet resistance value $R_s$ [Ω/□] at 100° C.

In addition, as to the dark current in the resistive film, the electrical conductivity σ (373.15) at 100° C. determined based on the above-mentioned Arrhenius equation is substituted into the equation $\sigma(T) = (I(T)/V) \times (d/(L \times t))$ described above. In this manner, the dark current I [A] at 100° C. is obtained.

In the present invention, as to the electrical connection between the resistive film 6 and the cathode 2 as well as the anode 4, it is preferred that, as illustrated in FIG. 1A, at least one of the cathode 2 and the anode 4 include on the peripheral edge portion thereof an extending portion protruding in a longitudinal direction of the insulating tube 5, the extending portion being connected to the resistive film 6. As the connection means, the cathode 2 or the anode 4 as a metal member may be mechanically pressed to contact with the resistive film 6, or a conductive paste may be used for connection. The connection means is not particularly limited as long as electrical connection can be established.

Figure 1B:
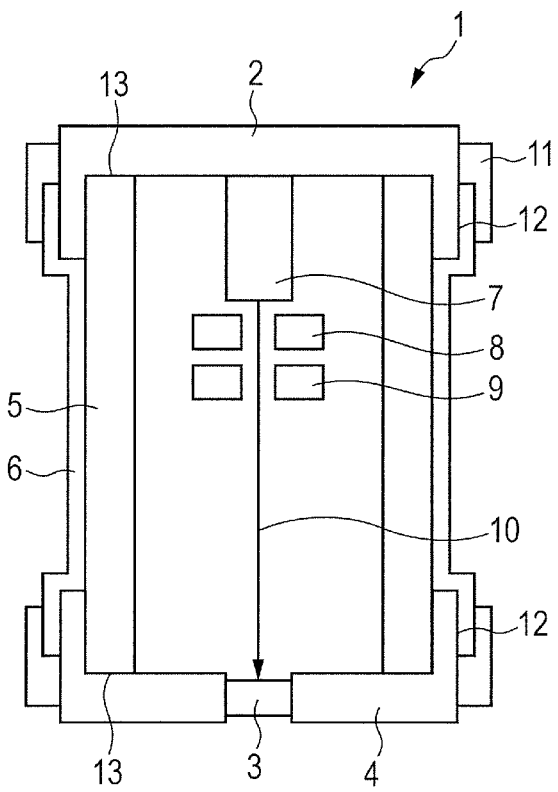

In addition, in FIG. 1A, the resistive film 6 is sandwiched between the insulating tube 5 and the extending portion of the cathode 2 or the anode 4. However, the extending portion may be sandwiched between the insulating tube 5 and the resistive film 6. In addition, as illustrated in FIG. 1B, it is also preferred to adopt a structure in which the extending portion of the cathode 2 or the anode 4 is sandwiched between the insulating tube 5 and the resistive film 6, and an end portion of the resistive film 6 connected to the extending portion is coated with conductive paste 11.

In the embodiment illustrated in FIG. 1A, an electrical connection portion 12 between the resistive film 6 and the anode 4 or the cathode 2 is positioned on an outer peripheral portion of the insulating tube 5. It is sufficient that the X-ray generating tube 1 of the present invention includes the resistive film 6 disposed at least on the outer peripheral portion of the insulating tube 5 so that the resistive film 6 is electrically connected to the anode 4 and the cathode 2. Other electrical connection forms are included in the present invention.

Figure 4A:
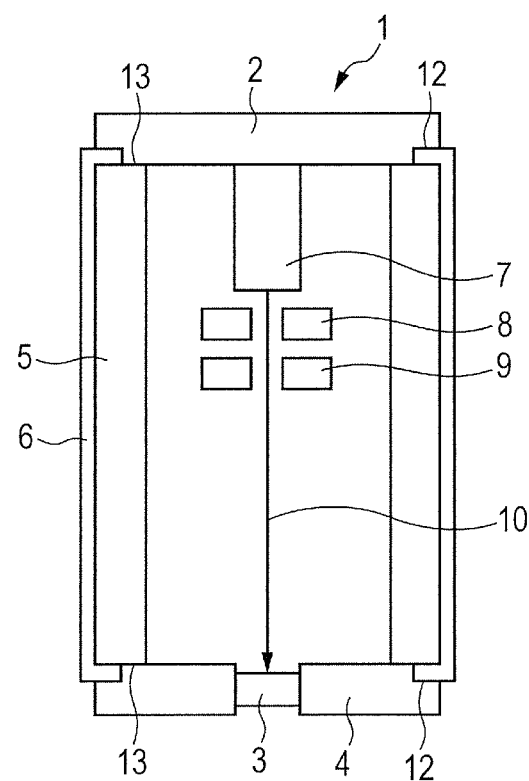
FIGS. 4A and 4B are cross-sectional schematic diagrams illustrating one another electrical connection form of the X-ray generating tube according to the present invention.
Figure 4B:
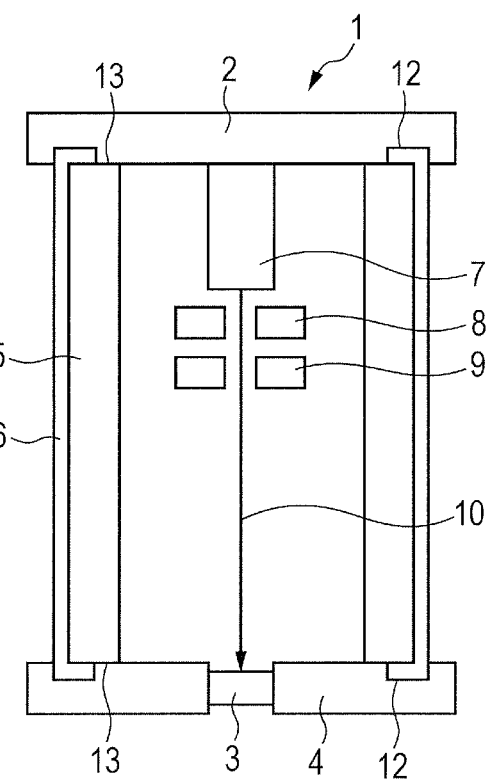
Figure 5:
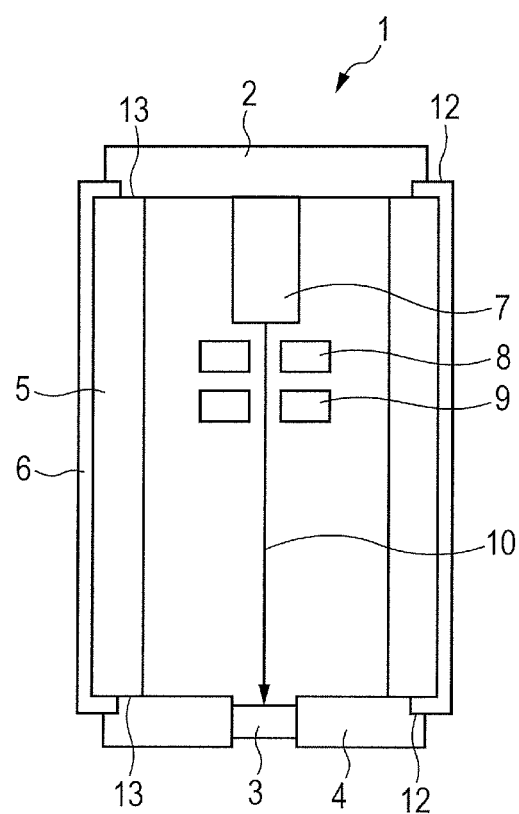
FIG. 5 is a cross-sectional schematic diagram illustrating $2^{nd}$ another electrical connection form of the X-ray generating tube according to the present invention.

For instance, as in each embodiment illustrated in FIG. 4A, FIG. 4B, or FIG. 5, the end surface 13 of the insulating tube 5 may include the electrical connection portion 12 between the resistive film 6 and the anode 4 or the cathode 2. Each embodiment illustrated in FIG. 4A, FIG. 4B, or FIG. 5 is an embodiment in which the anode 4 and the cathode 2 without the extending portion are connected to the insulating tube 5 including the resistive film 6 formed on the outer periphery and on the end surface 13 with silver braze.

The embodiment illustrated in FIG. 4A is an embodiment in which a radius of the outer periphery of the insulating tube 5 is the same as a radius of the outer periphery of the anode 4 and the cathode 2, and the resistive film 6 is connected to the anode 4 and the cathode 2 on the opposing end surfaces 13 of the insulating tube 5.

In addition, the embodiment illustrated in FIG. 4B is an embodiment in which the radius of the outer periphery of the anode 4 and the cathode 2 is larger than the radius of the outer periphery of the insulating tube 5, and the resistive film 6 is connected to the anode 4 and the cathode 2 on the opposing end surfaces 13 of the insulating tube 5. In this embodiment, the outer peripheral portions of the cathode 2 and the anode 4 protrude outward from the outer peripheral portion of the insulating tube 5 in the radial direction of the insulating tube 5.

In addition, the embodiment illustrated in FIG. 5 is an embodiment in which the radius of the outer periphery of the anode 4 and the cathode 2 is smaller than the radius of the outer periphery of the insulating tube 5, and the resistive film 6 is connected to the anode 4 and the cathode 2 on the opposing end surfaces 13 of the insulating tube 5. In this embodiment, the outer peripheral portions of the cathode 2 and the anode 4 protrude inward from the outer peripheral portion of the insulating tube 5 in the radial direction of the insulating tube 5.

In the embodiments illustrated in FIG. 4A, FIG. 4B, and FIG. 5, a distance between the anode 4 and the cathode 2 on the outer peripheral portion of the insulating tube 5 can be larger than that in the embodiment illustrated in FIG. 1A, and hence an average electric field in the tube axis direction on the outer peripheral portion can be reduced.

The inside of the X-ray generating tube 1 can be vacuumed by evacuating the air with use of an exhausting tube (not shown) and then by sealing the exhausting tube. It is possible to dispose a getter (not shown) in the X-ray generating tube 1 manufactured in this way for maintaining more appropriate vacuum.

Figure 2:
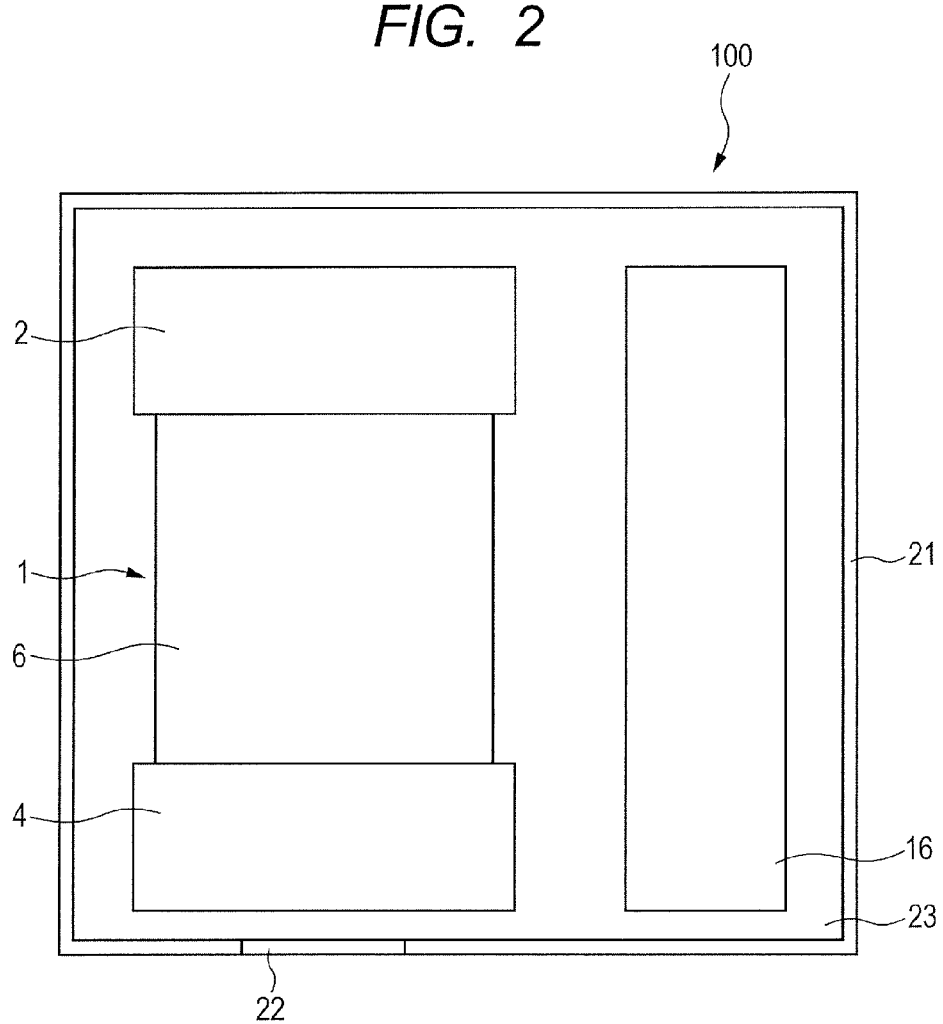
FIG. 2 is a cross-sectional schematic diagram illustrating a structure of an X-ray generating apparatus according to an embodiment of the present invention.

Next, an X-ray generating apparatus of the present invention is described. FIG. 2 is a cross-sectional schematic diagram illustrating an example of a structure of the X-ray generating apparatus including the X-ray generating tube 1 of FIG. 1A. As illustrated in FIG. 2, the X-ray generating apparatus of the present invention includes the X-ray generating tube 1 of the present invention and a container 21 for storing the X-ray generating tube 1. A rest space in the container 21 is filled with insulating liquid 23. In addition, the container 21 includes an X-ray emission window 22 for emitting the X-ray generated by the X-ray generating tube 1.

A drive circuit 16 including a circuit substrate and an insulating transformer (not shown) may be disposed inside the container 21. In the case where the drive circuit 16 is disposed, for instance, a predetermined voltage signal is applied to the X-ray generating tube 1 from the drive circuit 16 via wirings (not shown) so that generation of the X-ray can be controlled.

The container 21 only needs to have strength sufficient for a container and is made of a metal or plastic material. The container 21 includes the emission window 22 that transmits the X-ray for emitting the X-ray to the outside of the container 21. The X-ray emitted by the X-ray generating tube 1 passes through this emission window 22 and is emitted to the outside. The emission window 22 is made of glass, aluminum, beryllium, or the like.

It is preferred that the insulating liquid 23 have high electrical insulating property and high cooling performance, and be hardly degraded by heat. For instance, electrical insulation oil such as silicone oil, transformer oil, or fluorine-containing oil, and fluorine-containing insulating liquid such as hydro fluoro ether can be used.

Next, an X-ray imaging system according to an embodiment of the present invention is described with reference to FIG. 3.

Figure 3:
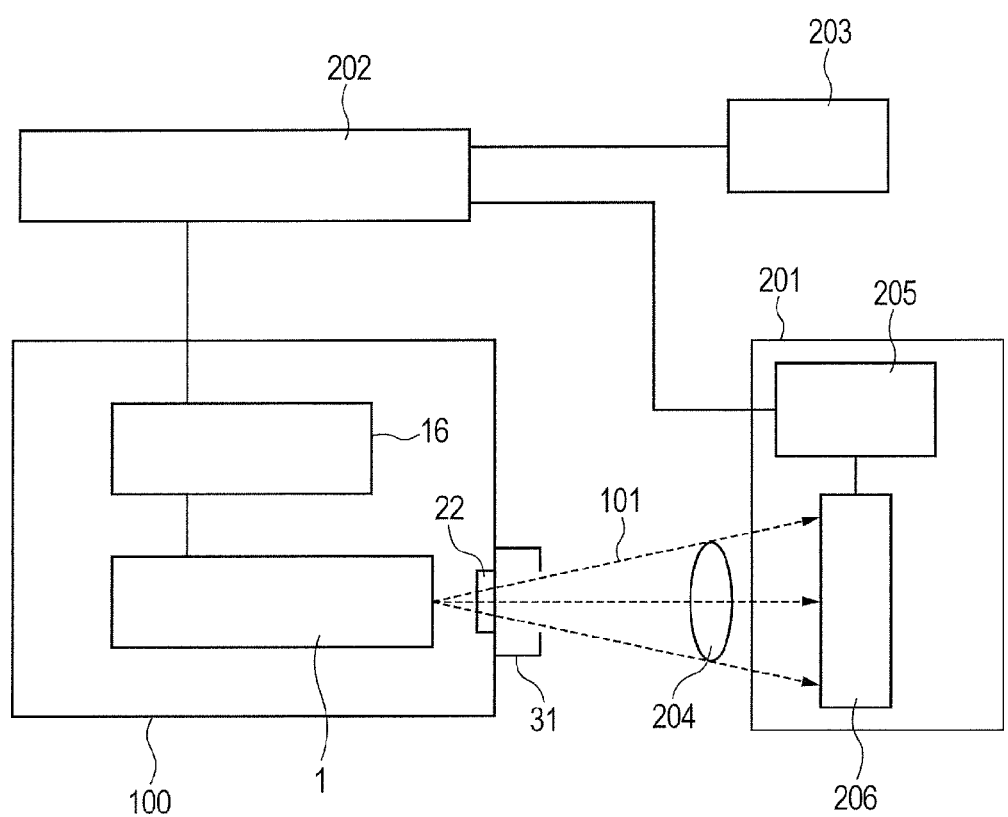
FIG. 3 is a block diagram schematically illustrating a structure of an X-ray imaging system according to an embodiment of the present invention.

As illustrated in FIG. 3, an X-ray generating apparatus 100 according to the present invention includes a movable diaphragm unit 31 disposed at a portion corresponding to the X-ray emission window 22 as necessary. The movable diaphragm unit 31 has a function of adjusting a radiation field of an X-ray 101 radiated from the X-ray generating apparatus 100. In addition, it is possible to use the movable diaphragm unit 31 having an additional function to perform simulation display of the radiation field of the X-ray using visible light.

A system control device 202 controls the X-ray generating apparatus 100 and an X-ray detecting device 201 in a coordinated manner. The drive circuit 16 outputs various control signals to the X-ray generating tube 1 under control by the system control device 202. This control signal controls a radiation state of the X-ray 101 emitted from the X-ray generating apparatus 100. The X-ray 101 emitted from the X-ray generating apparatus 100 passes through a subject to be investigated 204 and is detected by a detector 206. The detector 206 converts the detected X-ray into an image signal and outputs the image signal to a signal processing portion 205. Under control by the system control device 202, the signal processing portion 205 performs predetermined signal processing on the image signal and outputs the processed image signal to the system control device 202. The system control device 202 generates a display signal for controlling a display device 203 to display an image based on the processed image signal and outputs the display signal to the display device 203. The display device 203 displays an image based on the display signal as a photographed image of the subject to be investigated 204 on a screen.

The X-ray imaging system can be used for nondestructive inspection of an industrial product or pathological diagnosis of a human body or an animal body.

Example 1

The X-ray generating tube 1 illustrated in FIG. 1A was manufactured.

Slurry liquid made of a solution containing powder Kovar glass and acetic acid as main ingredients was sprayed and applied onto the outer peripheral surface of the cylindrical insulating tube 5 made or alumina, and was melted and welded at a glazing temperature of 1,000° C. so as to form the resistive film 6.

Next, the insulating tube 5 was sealed with the anode 4 made of Kovar metal with the target 3 mounted thereon and the cathode 2 made of Kovar metal with the electron emitting source 7 by using silver braze at 900° C. After that, the extending portions of the anode 4 and the cathode 2 were swaged toward the insulating tube 5 by an external force so that the anode 4 and the cathode 2 were electrically connected to the resistive film 6 at the extending portions overlapping the end portions of the resistive film 6.

An electric field was applied to the X-ray generating tube 1 having the above-mentioned structure in the creepage direction of the insulating tube 5 and the resistive film 6 so as to measure the IV characteristics by the measuring method described above. As a result, it was confirmed that the sheet resistance value of the resistive film 6 at 100° C. was $5 \times 10^{11} \Omega/\square$, and the sheet resistance value of the insulating tube 5 at 100° C. was $1 \times 10^{16} \Omega/\square$.

As a result, it was found that a dark current flowing between the cathode 2 and the anode 4 when a voltage of 100 kV was applied was 0.5 μA. It was confirmed that the dark current was sufficiently smaller than the tube current (10 mA) caused by the electron beam for generating an X-ray by the X-ray generating tube 1 and had no problem.

Further, a voltage of 100 kV was applied between the cathode 2 and the anode 4 so as to conduct an experiment in X-ray generation at a tube current of 10 mA. There was no occurrence of discharge, and it was possible to obtain stable X-ray radiation. In this example, there is also an effect of relieving concentration of the electric field to be lower at a triple point formed of the cathode 2, the resistive film 6, and the insulating liquid 23 than at a triple point formed at an end portion on the electrical insulation portion of the related-art electrical resistive film.

In addition, the reason why the X-ray generating tube 1 of this example was able to radiate a stable X-ray is estimated as follows. A variation and fluctuation of potential gradient in the inner space of the X-ray generating tube 1 sandwiched between the cathode 2 and the anode 4 is suppressed by a current field in the tube axis direction defined by the low resistive film 6. As a result, it is estimated that a locus of the electron beam 10 emitted from the electron emitting source 7 was stabilized.

Example 2

The X-ray generating tube 1 illustrated in FIG. 1B was manufactured.

The cylindrical insulating tube 5 made of alumina was sealed with the anode 4 made of Kovar metal with the target 3 mounted thereon and the cathode 2 made of Kovar metal with the electron emitting source 7 mounted thereon by using copper braze at 1,050° C. After that, the resistive film 6 similar to that of Example 1 was formed on the outer peripheral surface of the insulating tube 5 so that each end thereof overlapped with a portion of the extending portion of the anode 4 or the cathode 2. Further, the conductive paste 11 was applied onto the portions of the resistive film 6 where the extending portion of the anode 4 or the cathode 2 was overlapped so that end portions of the resistive film 6 were covered.

Next, the IV characteristics of the insulating tube 5 and the resistive film 6 were measured for the X-ray generating tube 1 having the structure described above similarly to Example 1, the sheet resistance value and the dark current at 100° C. were calculated, and the experiment in X-ray generation was conducted. As a result, the same appropriate result as in Example 1 was obtained. A contact angle of a metal with respect to the connection cross section is milder at a triple point formed of the conductive paste 11, the resistive film 6, and the insulating liquid 23 of this example than at a triple point at which the resistive film 6 is directly connected to the cathode 2 or the anode 4. Therefore, there is also an effect of relieving concentration of the electric field.

In addition, also in the X-ray generating tube 1 of this example, it was possible to obtain stable radiation of an X-ray.

According to the present invention, the surface of the insulating tube is covered with the resistive film having a lower sheet resistance value than the insulating tube, and the cathode and the anode are electrically connected. Thus, electrification on the surface of the conventional insulating tube can be prevented, and excessive potential gradient can be relieved. Therefore, it is possible to provide the X-ray generating tube with a simple structure, which has the improved withstand voltage obtained by suppressing occurrence of discharge. In addition, it is possible to provide the X-ray generating apparatus and the X-ray imaging system having high reliability by using the X-ray generating tube.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Applications No. 2013-118467, filed Jun. 5, 2013, and No. 2013-246985, filed Nov. 29, 2013, which are hereby incorporated by reference herein in their entirety.

What is claimed is:

1. An X-ray generating tube comprising:
   an insulating tube extending along a tube axis and having a pair of tube end portions;
   a cathode having an electron emitting source, the cathode being secured to one of the tube end portions;
   an anode having a target, the anode being secured to the other of the tube end portions; and
   a resistive layer disposed on an outer periphery of the insulating tube, the resistive layer having a lower sheet resistance than a sheet resistance of the insulating tube,
   wherein each of the cathode and the anode is connected to the resistive layer, respectively.

2. The X-ray generating tube according to claim 1, wherein a dark current at 100° C. when a voltage of 100 kV is applied between the cathode and the anode is 0.1 µA or more to 10 µA or less.

3. The X-ray generating tube according to claim 1, wherein at least one of the cathode and the anode comprises an extending portion protruding from the peripheral edge portion in a longitudinal direction of the insulating tube; and
   wherein the resistive layer is connected to the extending portion.

4. The X-ray generating tube according to claim 3, wherein the resistive layer is sandwiched between the extending portion and the insulating tube.

5. The X-ray generating tube according to claim 3, wherein the extending portion is sandwiched between the resistive layer and the insulating tube.

6. The X-ray generating tube according to claim 5, wherein an end portion of the resistive layer joined to the extending portion is covered with a conductive paste.

7. The X-ray generating tube according to claim 3, wherein an electrical connection portion between the resistive layer and the at least one of the cathode and the anode is positioned on an outer peripheral portion of the insulating tube.

8. The X-ray generating tube according to claim 1, wherein an electrical connection portion between the resistive layer and at least one of the cathode and the anode is positioned on an end surface of the insulating tube.

9. The X-ray generating tube according to claim 1, wherein the insulating tube is made of ceramic, and the resistive layer is made of a glass material.

10. The X-ray generating tube according to claim 9, wherein the insulating tube is made of alumina, and the resistive layer is made of glaze.

11. The X-ray generating tube according to claim 1, wherein a specific resistance of the insulating tube at 100° C. is $1 \times 10$ Ωm or more to $1 \times 10^{14}$ Ωm or less; and
   wherein $R_s2/R_s1$ is $1 \times 10^{-5}$ or more to $1 \times 10^{-1}$ or less, where $R_s1$ represents a sheet resistance value of the insulating tube at 100° C., and $R_s2$ represents a sheet resistance value of the resistive layer at 100° C.

12. The X-ray generating tube according to claim 1, wherein the outer periphery of the insulating tube is an outer periphery of the X-ray generating tube.

13. The X-ray generating tube according to claim 1, wherein the resistive layer defines a space electric field between the cathode and the anode.

14. The X-ray generating tube according to claim 1, wherein the anode comprises an end window including a transmissive target.

15. An X-ray generating apparatus comprising:
   the X-ray generating tube according to claim 1; and
   a container for storing the X-ray generating tube,
   wherein the container comprises an emission window for emitting X-ray generated by the X-ray generating tube, and a rest space inside the container storing the X-ray generating tube is filled with insulating liquid.

16. The X-ray generating apparatus according to claim 1, wherein the insulating liquid comprises at least one of silicone oil, transformer oil, and fluorine-containing oil.

17. An X-ray imaging system comprising:
   the X-ray generating apparatus according to claim 1;
   an X-ray detecting device configured to detect X-ray emitted from the X-ray generating apparatus and passing through a subject to be investigated; and
   a control device configured to control the X-ray generating apparatus and the X-ray detecting device in a coordinated manner.

18. An X-ray generating tube comprising:
   an insulating tube extending along a tube axis and having a pair of tube end portions;
   a cathode having an electron emitting source, the cathode being secured to one of the tube end portions;
   an anode having a target, the anode being secured to the other of the tube end portions; and
   a resistive layer disposed on an outer periphery of the insulating tube, the resistive layer having a lower sheet resistance than a sheet resistance of the insulating tube,
   wherein the resistive layer is connected to each of the cathode and the anode such that a variation and fluctuation of potential gradient in the inner space of the X-ray generating tube is suppressed by a current field along the tube axis direction defined by the resistive layer.

19. The X-ray generating tube according to claim 18, wherein a dark current at 100° C. when a voltage of 100 kV is applied between the cathode and the anode is 0.1 µA or more to 10 µA or less.

20. The X-ray generating tube according to claim 18, wherein at least one of the cathode and the anode comprises an extending portion protruding from the peripheral edge portion in a longitudinal direction of the insulating tube; and
   wherein the resistive layer is connected to the extending portion.

21. The X-ray generating tube according to claim 20, wherein the resistive layer is sandwiched between the extending portion and the insulating tube.

22. The X-ray generating tube according to claim 20, wherein the extending portion is sandwiched between the resistive layer and the insulating tube.

23. The X-ray generating tube according to claim 22, wherein an end portion of the resistive layer joined to the extending portion is covered with a conductive paste.

24. The X-ray generating tube according to claim 20, wherein an electrical connection portion between the resistive layer and the at least one of the cathode and the anode is positioned on an outer peripheral portion of the insulating tube.

25. The X-ray generating tube according to claim 18, wherein an electrical connection portion between the resistive layer and at least one of the cathode and the anode is positioned on an end surface of the insulating tube.

26. The X-ray generating tube according to claim 18, wherein the insulating tube is made of ceramic, and the resistive layer is made of a glass material.

27. The X-ray generating tube according to claim 26, wherein the insulating tube is made of alumina, and the resistive layer is made of glaze.

28. The X-ray generating tube according to claim 18, wherein a specific resistance of the insulating tube at 100° C. is $1 \times 10^{14}$ Ωm or more to $1 \times 10^{14}$ Ωm or less; and wherein $R_s2/R_s1$ is $1 \times 10^{-5}$ or more to $1 \times 10^{-1}$ or less, where $R_s1$ represents a sheet resistance value of the insulating tube at 100° C., and $R_s2$ represents a sheet resistance value of the resistive layer at 100° C.

29. The X-ray generating tube according to claim 18, wherein the outer periphery of the insulating tube is an outer periphery of the X-ray generating tube.

30. The X-ray generating tube according to claim 18, wherein the resistive layer defines a space electric field between the cathode and the anode.

31. The X-ray generating tube according to claim 18, wherein the anode comprises an end window including a transmissive target.

32. An X-ray generating apparatus comprising:
the X-ray generating tube according to claim 18; and
a container for storing the X-ray generating tube,
wherein the container comprises an emission window for emitting X-ray generated by the X-ray generating tube, and a rest space inside the container storing the X-ray generating tube is filled with insulating liquid.

33. The X-ray generating apparatus according to claim 32, wherein the insulating liquid comprises at least one of silicone oil, transformer oil, and fluorine-containing oil.

34. An X-ray imaging system comprising:
the X-ray generating apparatus according to claim 32;
an X-ray detecting device configured to detect X-ray emitted from the X-ray generating apparatus and passing through a subject to be investigated; and
a control device configured to control the X-ray generating apparatus and the X-ray detecting device in a coordinated manner.

35. The X-ray generating tube according to claim 18, wherein the resistive layer is electrically connected to each of the cathode and the anode.

36. The X-ray generating tube according to claim 18, wherein the resistive layer is overlaid with a part of each of the cathode and the anode.

* * * * *